United States Patent [19]
Weber et al.

[11] Patent Number: 4,890,618
[45] Date of Patent: Jan. 2, 1990

[54] NERVE-STIMULATING DEVICE FOR AUDITORY PROSTHESIS

[75] Inventors: Jean-Luc M. Weber, Salon de Provence; Serge Bloch, Aix en Provence; Jean-Claude Noack, Cabries; Claude-Henri Chouard, 10, Boulevard Flandrin, 76016 Paris; Patrick MacLeod, 424 Avenue de la Division Leclerc, 92290 Chatenay Malabry, all of France

[73] Assignees: Bertin & CIE, Plaisir Cedex; Claude-Henri Chouard, Paris; Patrick MacLeod, Chatenay-Malabry, all of France

[21] Appl. No.: 906,520

[22] Filed: Sep. 12, 1986

[30] Foreign Application Priority Data
Sep. 12, 1985 [FR] France .................. 85 13528
Sep. 12, 1985 [FR] France .................. 85 13529

[51] Int. Cl.⁴ .............................................. A61N 1/18
[52] U.S. Cl. .............................. 128/420.6; 128/784

[58] Field of Search ............ 128/420.5, 420.6, 423 R, 128/783, 784, 789; 381/68, 68.4, 68.6; 181/126, 129, 130, 134, 135

[56] References Cited
U.S. PATENT DOCUMENTS

| | | | |
|---|---|---|---|
| 3,752,939 | 8/1973 | Bartz | 128/420.6 X |
| 4,289,935 | 9/1981 | Zollner et al. | 128/420.6 X |
| 4,419,995 | 12/1983 | Hochmair et al. | 128/419 R |
| 4,510,936 | 4/1985 | Fourcin et al. | 128/420.6 X |
| 4,532,930 | 8/1985 | Crosby et al. | 128/420.6 X |
| 4,592,359 | 6/1986 | Galbraith | 128/420.6 X |
| 4,593,696 | 6/1986 | Hochmair et al. | 128/420.6 |
| 4,611,596 | 9/1986 | Wasserman | 128/420.6 X |

Primary Examiner—Francis Jaworski
Attorney, Agent, or Firm—A. W. Breiner

[57] ABSTRACT

A single-channel nerve stimulating device for auditory prosthesis for improving the conversational capacity of a profoundly deaf person is described. The single-channel device of simple construction provides detailed information to the patient's nervous system. The device comprises a microphone designed to pick up a sound signal and electronic processor which converts the sound signal into an electrical signal.

12 Claims, 3 Drawing Sheets

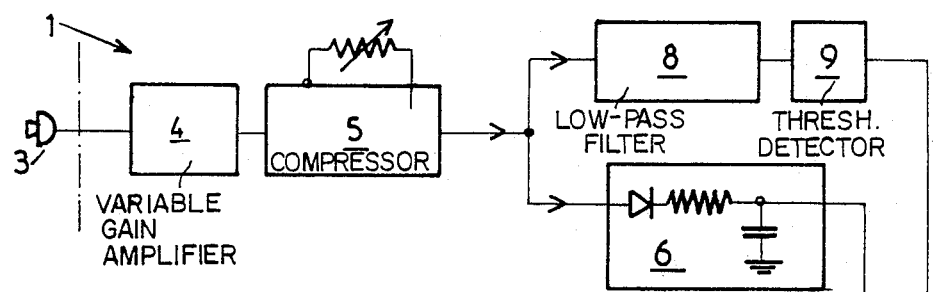
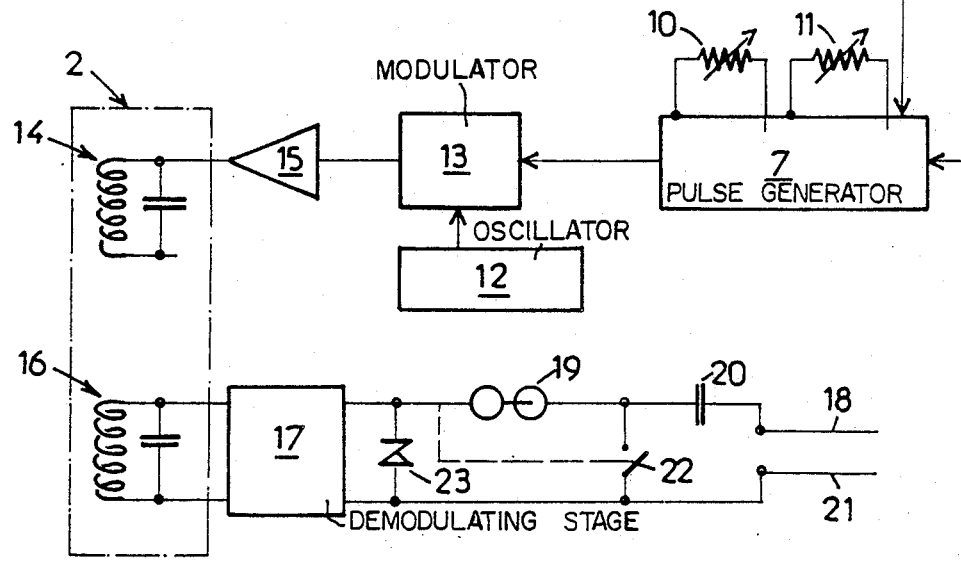
FIG.:1
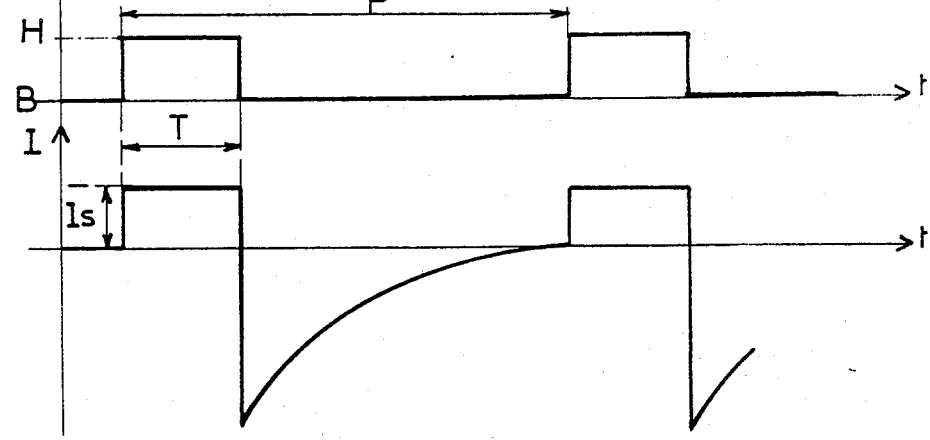
FIG.:2

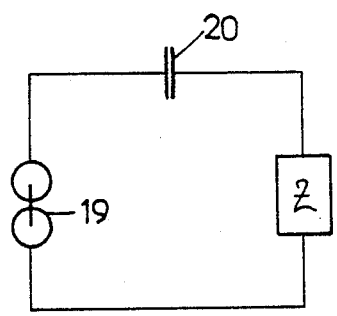
FIG.:3
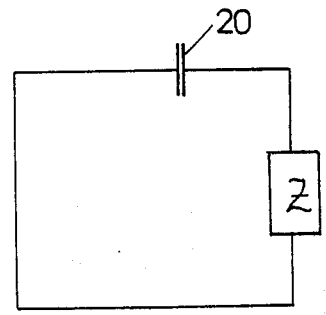
FIG.:4
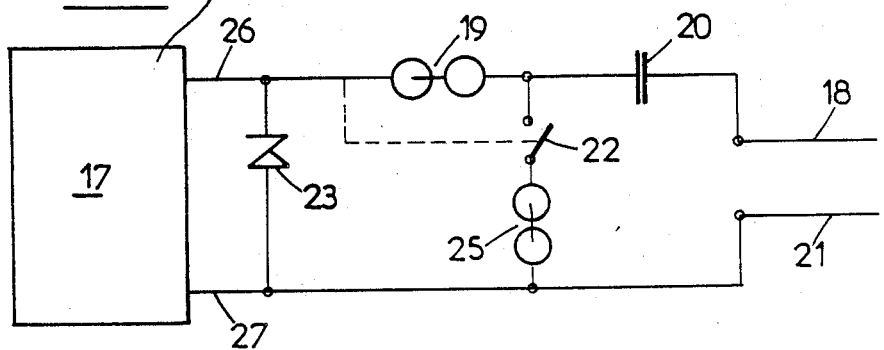
FIG.:5
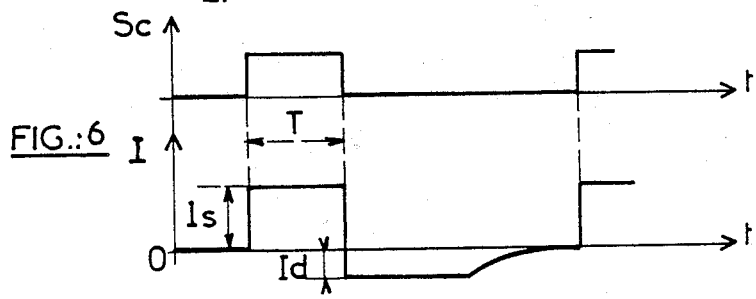
FIG.:6
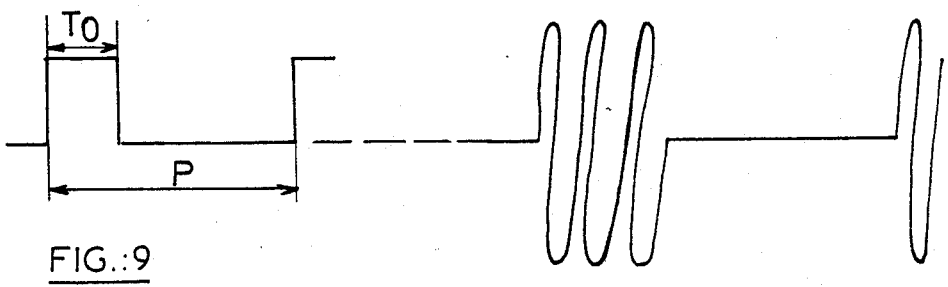
FIG.:9

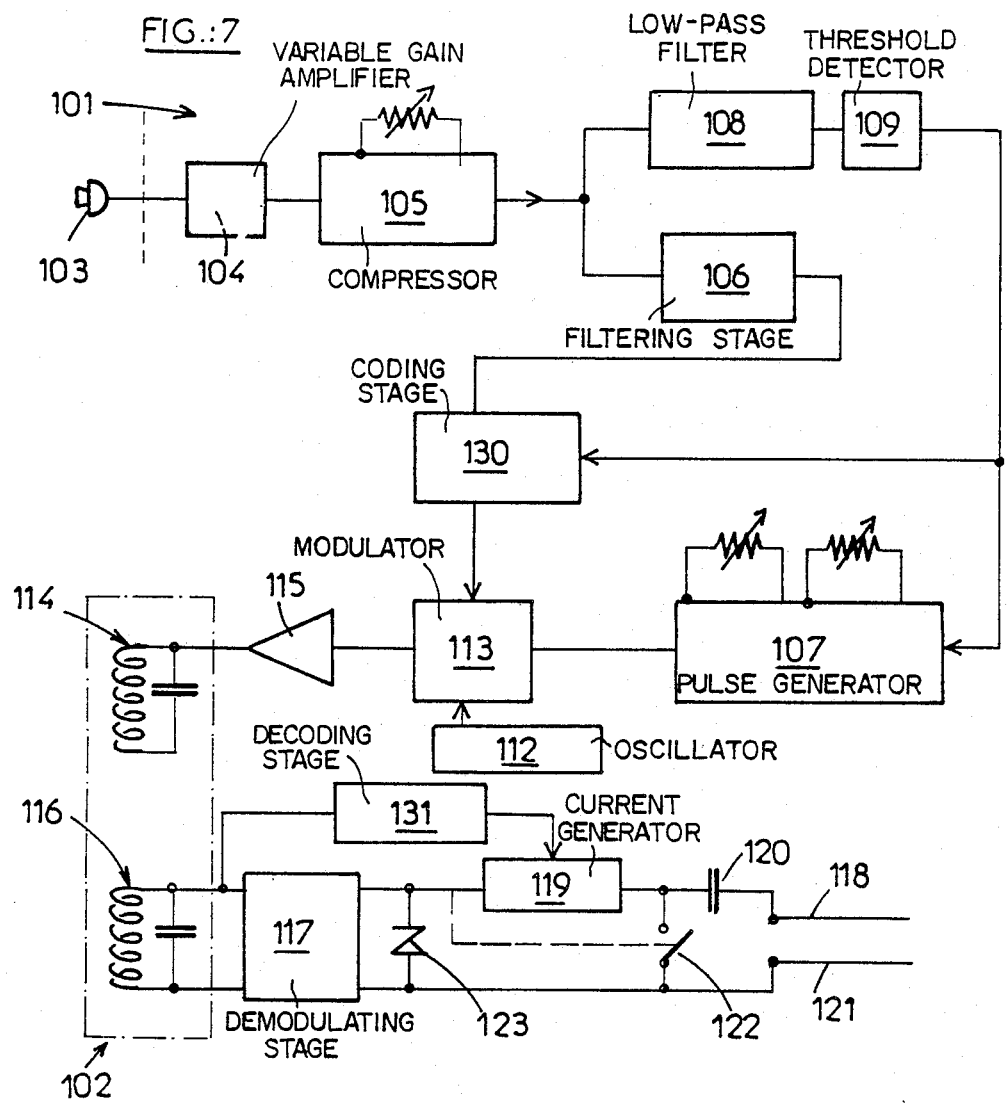
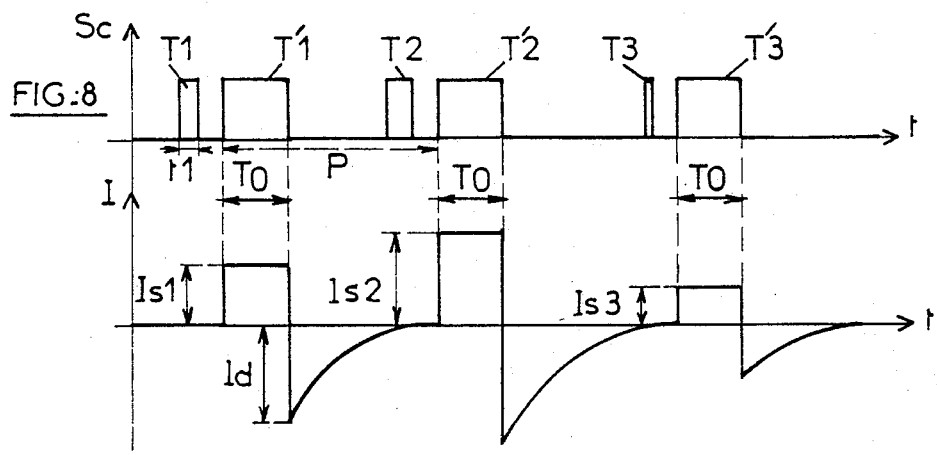

NERVE-STIMULATING DEVICE FOR AUDITORY PROSTHESIS

The invention relates to a nerve-stimulating device for auditory prosthesis.

The mechanical vibrations forming sounds, after being transmitted to the fluids of the inner ear by the action of the drum and ossicles, excite the ciliary sensory cells of the cochlea. These ciliary cells convert the mechanical vibrations into electrophysiological signals which they transmit to the dendrites of the fibers of the auditory nerve carrying these signals to the brain.

Where the profoundly deaf, whose ciliary sensory cells are deficient, are concerned, the conventional hearing aid devices are ineffective because they merely increase to a greater or lesser extent the mechanical energy supplied to the ear, and they have to be replaced by a device which stimulates the auditory nerve directly by means of an electrical current.

Of the nerve-stimulating devices for auditory prosthesis which are known at the present time, a distinction is made between those called "multiple-channel" and those of the "single-channel" type.

The first are based on the finding that a complex soundwave comprising numerous sinusoidal components of different frequencies gives rise to vibration peaks distributed over the basilar membrane which carries the ciliary cells within the cochlea. This membrane vibrates at a maximum amplitude to a point which is in mechanical resonance with the frequency of the sound, the high frequencies causing the base of the cochlear spiral to vibrate, and low frequencies causing the top of the latter to vibrate. Multiple-channel stimulating devices utilize this property by means of a system with n electrodes implanted in the cochlea, each electrode being assigned to one of n consecutive groups of fibers of the auditory nerve. These electrodes are excited selectively via independent channels, to which certain frequency bands are assigned, so that these independent channels as a whole make it possible to cover a predetermined region of the audible sound spectrum.

These multiple-channel devices for stimulating the cochlear nerve, an example of which will be found in the Patent FR-A-2,383,657, are efficient, but have a high cost price because they are so sophisticated. Moreover, the operation to implant the bundle of n electrodes inside the cochlea is very difficult and has to be carried out once and for all in view of the risks of damage to certain very delicate internal tissues of the cochlea which would arise if it were repeated. Consequently, the implantation of these expensive but effective multiple-channel devices is reserved for patients whose electro-physiological characteristics suggest that they have sufficient residual hearing to utilize its possibilities to the full.

If the patients are incapable of making use of the wealth of spectral information supplied by the multiple-channel devices, it is generally preferable to resort to single-channel devices which are much less costly and much less difficult to implant. These devices comprise a single stimulation electrode arranged in the middle ear either near the base of the cochlea or on the outside of the latter. Like the multiple-channel devices, single-channel devices comprise a microphone designed to pick up a sound signal, an electronic processor which converts the sound signal into electrical signals, and means of transmitting these electrical signals to the electrode stimulating the auditory nerve.

A single-channel device for stimulating the auditory nerve is described, in particular, in the Patent Application EP-A-0,076,069. Such a device makes it possible for patients whose deafness is either congenital or acquired in adulthood to perceive the rhythm and intensity of the sound, but it does not provide sufficient information to the nervous system to enable a deaf person to identify the person speaking to him in a conversation involving several people, without resorting to lip-reading.

The Patent GB-A-2,133,697 also makes known a single-channel device comprising a transducer designed to pick up a sound signal, a low-pass filter, a logarithmic amplifier intended for compressing the filtered signal coming from the transducer, and a peak detector making it possible to extract the fundamental frequency from a speech signal, that is to say the voicing or pitch of the voice.

By extracting the voicing, this device makes it possible to restore to a patient equipped with it the "coloring" of the sound signal emitted by the speaker.

However, it has a serious disadvantage in that the stimulation signal is composed of pulses, the length of which is substantially equal to half the fundamental period of the speech signal. In other words, the lower the speaker's voice, the more intense the sound perceived by the patient, and vice versa, but this does not conform to the reality of the physical phenomena perceived by persons enjoying normal hearing.

In fact, if several speakers are positioned at different distances from a patient, the latter risks being led into error since the sound perceived as being the loudest will not necessarily come from the speaker nearest to him.

Moreover, this device comprises relatively complex means intended to make a distinction between voiced signals and unvoiced signals. When an unvoiced sound is detected, a stimulation having predetermined characteristics is applied to the patient. The same thing will occur if, for any reason, the device has not detected a voiced signal and has identified it as unvoiced. In both cases, the information transmitted to the patient is therefore arbitrary.

The objective of the invention is to improve the conversational capacity of the profoundly deaf by means of a single-channel device of simple construction which provides more detailed information to the patient's nervous system than that to which they have access with conventional single-channel devices.

To achieve this, the subject of the invention is a single-channel nerve-stimulating device for auditory prosthesis, which comprises a microphone designed to pick up a sound signal, an electronic processor which converts this sound signal into an electrical signal and which comprises circuits making it possible to extract from a speech signal of a speaker a component representing the voicing and to generate an electrical signal having the same frequency as the said component, and means of transmitting the said electrical signal to a circuit exciting an electrode for stimulating an auditory nerve, wherein the electronic processor comprises circuits for modulating and/or coding the said electrical signal as a function of the total energy of the sound signal picked up, in order to apply a stimulation signal representing both the total energy and a possible voicing of the sound signal to the stimulation electrode by means of the exciting circuit.

Preferably, the exciting circuit comprises a current source emitting constant-current stimulation pulses having a predetermined electrical charge as a function of the total energy of the sound signal, and means of generating, following each stimulation pulse of a given polarity, a pulse neutralizing electrochemical reactions which has an opposite polarity and the same electrical charge as the preceding stimulation pulse.

This preferred embodiment makes it possible to render reversible and harmless the complex electrochemical reactions which are produced in the biological tissues as a result of the electrical stimulation and which, with the conventional devices, are capable of modifying the electrical characteristics of the stimulus.

The invention is used particularly for the treatment of profound deafness and buzzing in the ears.

Other features and advantages of the invention will emerge more clearly from a reading of the following description given by way of non-limiting example, with reference to the accompanying drawings in which:

FIG. 1 is a block diagram of a first embodiment of the nerve-stimulating device.

FIG. 2 is a graph showing the form of the control signal and of the current delivered to the stimulation electrode of the device of FIG. 1.

FIG. 3 is an equivalent electrical diagram of part of the exciting circuit of the device during the stimulation phases.

FIG. 4 is an equivalent diagram of part of the exciting circuit of the device during the neutralization phases.

FIG. 5 is an electrical diagram of an alternative form of the exciting circuit of the device of FIG. 1.

FIG. 6 is a graph similar to that of FIG. 2, showing the form of the current obtained with the exciting circuit of FIG. 5.

FIG. 7 is a block diagram of a second embodiment of the nerve-stimulating device.

FIG. 8 is a graph showing the form of the control signal and of the pulse current generated by the exciting circuit of the device of FIG. 7, and FIG. 9 is a graph showing forms of signals illustrating an alternative embodiment of the device of FIG. 7.

FIG. 1 shows the circuits forming the transmitter subassembly 1 and the receiver subassembly 2 of the device.

The transmitter subassembly 1 comprises a microphone 3 which is intended to pick up a sound signal and the output of which is applied to an amplifier 4 with a gain variable between, for example, 30 and 1000. The output of the variable-gain amplifier 4 is applied to the input of a compressor 5, the function of which is to adapt the dynamics of the sound information signal to the dynamics of the ear. Thus, for example, a noise varying between 40 dBA (threshold of perception) and 100 dBA (pain threshold) can be compressed in the circuit 5 to obtain a variation of 6 dB for the energy of the electrical stimulation signal, this compression of course being proportional, at each moment, to the instantaneous energy of the sound picked up, so as not to distort the scale of sensations in the brain (such a compression being carried out by the drum and the middle ear in people with normal hearing). The compressor 5 can comprise, for example, an electronic circuit with a logarithmic transfer function. The output of the compressor 5 is applied to the input of a stage 6 for rectifying and filtering the compressed signal, generating a voltage representing the compressed energy of the original sound signal in order to control a pulse generator 7.

The output of the compressor 5 is also applied to the input of a low-pass filter 8, such as a third-order filter having a cut-off frequency of a few hundred Hertz, for example approximately 400 Hertz. The output signal from the filter 8 is coupled to the input of a detector 9, the threshold of which is variable so as to take into account only signals representing a sound signal having a minimum level of, for example, 40 dBA. It will be noted, however, that the detector 9 could also be located upstream of the filter 8 or compressor 5.

The electrical signal which has passed through the filter 8 and the detector 9 corresponds to the fundamental frequency of the sound signal applied to the microphone 3, that is to say, when a speech signal is concerned, it represents the voicing of the speech of the person speaking. This voicing signal is applied to the trigger input of the pulse generator 7 which, in synchronism with the voicing signal, generates rectangular pulses, the width of which is a function of the sound volume signal coming from the rectifying and filtering stage 6. This pulse generator comprises two potentiometers 10 and 11, of which one 10 allows the medical team, when implanting the device in a patient, to adjust the maximum length of the pulses transmitted by the generator 7 and the other 11 offers the patient the possibility of adjusting the "volume" during use. Thus, the patient can, by himself, reduce the maximum length of the pulses, for example to a third of the maximum length set by the medical team.

The output signal Sc from the pulse generator 7 is shown in FIG. 2, where T represents the pulse length and P the period of the voiced signal. Preferably, the adjustments made by means of the potentiometer 10 are such that T is always between approximately 5 and 500 $\mu$s and varies between two extremes according to a logarithmic law for sound levels ranging from approximately 40 dBA to 80 dBA. A high-frequency signal, for example of 3 MHz, emitted by an oscillator 12 is modulated in a modulator 13 by the pulse train supplied by the generator 7. The resulting signal is applied to a transmitting antenna 14 by means of a power stage 15.

The signal transmitted by the antenna 14 is received by the receiver subassembly 2 by means of a receiving antenna 16 tuned to the frequency of the carrier wave supplied by the oscillator 12. The receiving antenna 16 is followed by a demodulating stage 17 which rectifies and filters the signal received and which re-establishes a pulse signal according to that of FIG. 2. One of the output terminals of the stage 17 is connected to the stimulation electrode 18 by means of a constant-current source 19 and a capacitor 20, whilst its other terminal is connected to the ground electrode 21 associated with the stimulation electrode 18. An electronic switch 22, controlled by the output signal of the stage 17, is connected between, on the one hand, the point common to the current source 19 and to the capacitor 20 and, on the other hand, the shell electrode 21. This electronic switch which can, for example, comprise a conventional assembly with two transistors is opened when the output signal from the stage 17 (see FIG. 2) is at its high level and the current source 19 excites the stimulation electrode 18. It closes when the signal passes to its low level, thus allowing the capacitor 20 to be discharged via the circuit comprising the electronic switch 22 and the inter-electrode gap. Finally, a Zener diode is connected between the output terminals of the stage 17, in order to limit the possible over-voltages which may occur between these terminals to a permissible value, for example 20 volts.

Conventionally, the receiver subassembly 2 forming the exciting circuit is intended to be implanted between the skin and the skull of a patient near one of his ears. The stimulation electrode 18 can be located either in the cochlea or outside the latter, provided that the cochlea is within the electrical field induced by the active electrode and the shell electrode. The external transmitting subassembly 1 is worn by the patient in such a way that the transmitting antenna is located opposite the receiving antenna. The microphone 3 is preferably fastened, together with the transmitting antenna 14, either to a molding within the ear or to an ear contour. These two elements are connected by means of an electrical lead to a box which is carried by the patient in one of his pockets and which contains the other circuits of the transmitter subassembly.

During operation, a speech signal picked up by the microphone 3 is processed by the stages 4 to 9 which supply the signal Sc of FIG. 2 at the output of the pulse generator 7. After being modulated, amplified, transmitted and demodulated, this same signal Sc controls the constant-current source 19. When the signal Sc passes to its high level H, the current source 19 is made conductive, whilst the electronic switch 22 is open. The equivalent electrical diagram of the exciting circuit is then that shown in FIG. 3, in which the current source 19 delivers a constant current to an impedance Z, symbolizing the impedance of the biological tissues located between the electrodes 18 and 21, by means of the capacitor 20. As shown by the graph in FIG. 2, in which the second curve I represents the behavior of the current in the stimulation electrode 18, the latter is fed with a constant current of predetermined intensity is for the time T during which the control signal is at its high level. When the latter passes to its low level B, it blocks the current source 19 and closes the switch 22. The equivalent electrical diagram of the exciting circuit is then that shown in FIG. 4, where the capacitor 20 is connected in series to the impedance Z by means of the electrodes 18 and 21. At the moment when the switch 22 closes, the capacitor 20 discharges into the impedance Z, thus resulting in a reversal of the direction of the current, as shown in FIG. 2, until there appears a new control-signal pulse Sc which causes a new cycle involving the conduction of the current source 19, the charging of the capacitor 20 and then the discharge of the latter following the closure of the switch 22.

The result of the foregoing is that a constant current of predetermined intensity Is is transmitted to the biological tissues to be stimulated, for a time T proportional to the control value, this corresponding to a charge $Q = Is \times T$ in the capacitor 20 and in the tissues. This method of stimulation by regulated constant current makes it possible to overcome both differences in impedance which the biological tissues can have from one individual to another and impedance drifts in time of the electrical circuits, attributable, for example, to changes in the position or electrical characteristics of the electrodes, to aging of the electronic components of the implant, to changes in the position of the transmitting antenna in relation to the receiving antenna, etc. Furthermore, since the capacitor discharged after each charge phase or alternation, it emerges that the mean value of the current in the stimulation electrode is zero over a full period or, in other words, over a full period there is a perfect balance of the electrical charges transmitted to the auditory nerve, this being of great importance from a physiological point of view.

Another advantage of the device described above is in the method of processing the sound signal which, on the basis of a speech signal, makes it possible to excite the auditory nerve of a patient by means of an electrophysiological signal representing both the amplitude and the voicing of the speech. In other words, this electrophysiological signal is free of the information associated with acutual elocution, whilst at the same time preserving the voicing which is highly characteristic of an individual. It can therefore be accepted that, with a certain amount of training, the above-described device should enable a profoundly deaf person to ascertain the particular person who is speaking, not be seeing the movement of his lips, but by recognizing his voicing directly. Of course, this ability will not free the patient from the need to resort to lip reading to give the spoken words an intelligible content, but it constitutes a significant advance in relation to single-channel devices of the prior art which only allowed the patients to perceive a complex noise of modulated amplitude difficult to identify.

The alternative embodiment of the exciting circuit shown in FIG. 5 differs from that in FIG. 1 only in the presence of a discharge-current regulator 25 connected in series between the electronic switch 22 and the shell electrocde 21. This regulator makes it possible to limit the maximum value of the current in the shell electrode 21 to a value Id during the discharge phase of the capacitor 20, as shown on the negative part of the curve I of FIG. 6. Otherwise, the exciting circuit of FIG. 5 is identical in all respects to that of FIG. 1, the optional Zener diode 23, as in the latter, ensuring protection of the tissues against the possible over-voltages which may occur between the terminals 26 and 27.

Referring now to FIG. 7, in which the same references as in FIG. 1, but increased by 100, have been used to designate the same components, this second embodiment differs from that of FIG. 1 only as regards the method of coding the volume of the sound signal picked up. Thus, the rectifying and filtering stage 106 is connected not to the pulse generator 107, but to the modulator 113 by means of a current-amplitude coding stage 130.

The pulse signal resulting from this coding is shown in demodulated form in FIG. 8. It comprises a first current coding pulse T1, of which the length t1 variable, for example, from 1 to 5 $\mu$s is proportional to the intensity of the current to be generated by the source 119, and a second pulse T'1, of constant length T0 in this particular use, during which the current, the intensity of which is determined by the pulse T1, is delivered to the electrode 118. The coding stage 130 functions in a similar way to the pulse generator 7 and emits the pulse T1 of a length t1 proportional to the sound volume under the control of the voicing signal applied to its trigger input. The pulse generator 107 emits the pulse T'2 of constant length T0 with a predetermined delay in relation to the rising edge of the pulse T1. Consequently, the time P separating the rising edges of two consecutive pulses T'1, T'2, T'3 represents, as in the first embodiment, the fundamental period of the speech signal. After modulation, this signal is transmitted to the receiving antenna 116.

A decoding stage 131 connected to the latter controls the current generator 119 so that it generates a current of intensity Is1, Is2, Is3 proportional to the length of the corresponding pulse T1, T2, T3. This constant current proportional to the volume of the sound signal picked up is delivered to the electrode 118 for the length T0, constant in this particular use, of the pulse T'1, T'2, T'3. Otherwise, the mode of operation of this second embodiment is completely identical to that of FIG. 1. It can be seen that this second embodiment also makes it possible to transmit a perfectly controlled amount of electricity to the auditory nerve.

FIG. 9 also shows, for future reference, signals illustrating an alternative form of the second embodiment. In this alternative form, the pulse generator 107 emits pulses of length T0, the period of recurrence T of which is that of the fundamental component of the sound signal picked up. The coding stage 130 determines, as a function of the intensity of the current to be generated, the amplitude of the carrier wave modulated by the output signal from the generator 107. At the transmitter subassembly level 102, the decoding stage 131 controls the current generator 119 so that it generates a current proportional to the amplitude of the carrier wave applied to it.

Of course, it is also possible to use other means, such as, for example, frequency modulation or phase modulation, to generate a current which is proportional to the volume of the sound signal and which will be transmitted to the stimulation electrode for a predetermined constant time. The feature common to all these various solutions is that it is possible to transmit a perfectly defined amount of electricity to the auditory nerve.

However, it should be understood that the invention is in no way limited to the use of this advantageous characteristic, and that the electrophysiological signal representing the voicing and volume of the speech signal picked up could also have a sinusoidal or other form variable not in terms of intensity or pulse width, but, for example, in terms of voltage.

We claim:

1. A single channel-stimulating device for an auditory prosthesis comprising:
   a single-channel electrode means for electrically stimulating an auditory nerve,
   transducer means for receiving a sound signal and providing a corresponding electrical input signal,
   patient externally worn electronic processor means connected to said transducer means for processing said electrical input signal, said processor means including
      first processing means including a low-pass filter for filtering said input electrical signal and producing a first output electrical signal having a frequency representative of the pitch of a voiced sound signal received by said transducer means,
      second processing means connected in parallel with said first processing means and including rectifying and filtering means for rectifying and filtering said electrical input signal and generating a second output signal having a level representative of the total energy of the sound signal received by said transducer means, and
      third processing means connected to said first and second processing means and including modulating and/or encoding means for generating an electrical control signal as a function of said first and second output electrical signals,
   a patient implantable electrical exciting circuit connected to said single-channel electrode means and driven by said electrical control signal for applying to said electrode means an electrical stimulation pulse signal which represents both the total energy and the pitch of a voiced sound signal received by said transducer means, and
   transmitting means for transmitting said electrical control signal from said processor means to said exciting circuit.

2. A device as claimed in claim 1 wherein said exciting circuit comprises:
   a current source connected to said stimulation electrode means and driven by said electrical control signal for producing said electrical stimulation pulse signal in which the pulse rate is equal to the frequency of the first output electrical signal and the electrical charge of each pulse is a function of the level of said second output electrical signal, and
   charge controlling means connected to said stimulation electrode means and driven by said control signal for generating, following each stimulation pulse of a given polarity of said electrical stimulation pulse signal, a neutralizing pulse which has an opposite polarity and the same electrical charge as the preceding stimulation pulse.

3. A device as claimed in claim 2 wherein the stimulation electrode means comprise a stimulation electrode and a ground electrode and the charge controlling means comprise a capacitor connected between the current source and the stimulation electrode and an electronic switch controlled by said transmitting means in order to connect the capacitor in series between the stimulation electrode and the ground electrode following each stimulation pulse.

4. A device as claimed in claim 3 wherein a regulator of the discharge current of the capacitor is connected in series between the electronic switch and the ground electrode.

5. A device as claimed in claim 3 wherein the current source and the capacitor are connected in series to the stimulation electrode, and the electronic switch is connected between, on the one hand, a point common to the current source and to the capacitor and, on the other hand, the ground electrode.

6. A device as claimed in claim 3 wherein said processor means produces a rectangular control signal and the current source and the switch are responsive to said rectangular control signal to respectively become conductive and open when said control signal is at a first level and to respectively become non-conductive and to close when said control signal is at a second level 7. A device as claimed in claim 1 wherein the electronic processor means comprises a variable-gain amplifier connected between said transducer and a compressor, the output of which is connected respectively to said first and second processing means.

8. A device as claimed in claim 7, including a generator means connected to the low-pass filter of said first processing means for applying pulses of the same frequency as said first output electrical signal to a stage coding the intensity of the current of the stimulation pulse signal as a function of the output signal from the rectifying and filtering means, the coding stage supplying the said control signal.

9. A device as claimed in claim 8 wherein the exciting circuit comprises a current source and a control-signal decoding stage which determines the intensity of the current supplied to the stimulation electrode by the current source for the length of the said pulses.

10. A device as claimed in either one of claims 8 and 9, wherein the said pulses have a constant length.

11. A device as claimed in claim 1 wherein said third processing means comprise a generator receiving said first and second output signals and supplying pulses of modulated length proportional to the level of said second output signal, with a pulse rate equal to the frequency of said first output signal.

12. A device as claimed in claim 11 wherein the exciting circuit comprises a current source which is driven by said control signal for supplying a current of predetermined constant intensity for the modulated length of the pulses output by said generator.

* * * * *